United States Patent
Pellegrini et al.

(10) Patent No.: US 12,115,090 B2
(45) Date of Patent: Oct. 15, 2024

(54) STENT GRAFT DELIVERY SYSTEM INCLUDING STENT GRAFT CUTTER

(71) Applicant: Medtronic Vascular Inc., Santa Rosa, CA (US)

(72) Inventors: Gianfranco M. Pellegrini, Santa Rosa, CA (US); Adam J. Shipley, San Rafael, CA (US); Mark L. Stiger, Santa Rosa, CA (US); Zachary E. Borglin, Petaluma, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 681 days.

(21) Appl. No.: 17/212,689

(22) Filed: Mar. 25, 2021

(65) Prior Publication Data

US 2022/0304837 A1     Sep. 29, 2022

(51) Int. Cl.
| | |
|---|---|
| *A61F 2/966* | (2013.01) |
| *A61F 2/07* | (2013.01) |
| *A61M 25/00* | (2006.01) |
| *A61M 25/01* | (2006.01) |

(52) U.S. Cl.
CPC ............ *A61F 2/966* (2013.01); *A61F 2/07* (2013.01); *A61F 2250/0071* (2013.01); *A61M 2025/0002* (2013.01); *A61M 2025/0166* (2013.01)

(58) Field of Classification Search
CPC ........... A61F 2/82–2/97; A61F 2/06–2002/077
See application file for complete search history.

(56) References Cited

U.S. PATENT DOCUMENTS

| | | | |
|---|---|---|---|
| 10,159,819 B2 | 12/2018 | Duffy et al. | |
| 2003/0135266 A1* | 7/2003 | Chew | A61F 2/91 623/1.16 |
| 2007/0265637 A1* | 11/2007 | Andreas | A61F 2/966 623/1.11 |
| 2009/0264987 A1 | 10/2009 | Gale | |
| 2010/0125323 A1 | 5/2010 | Berglund et al. | |
| 2012/0253471 A1 | 10/2012 | Tully et al. | |
| 2018/0161557 A1* | 6/2018 | DeGraaf | A61F 2/04 |

OTHER PUBLICATIONS

Extended European Search Report for Application No. 22163185.6, Jul. 19, 2022, 13 pages, Munchen, Germany.

* cited by examiner

*Primary Examiner* — Thomas McEvoy
(74) *Attorney, Agent, or Firm* — Medler Ferro Woodhouse & Mills PLLC

(57) ABSTRACT

A stent graft delivery system includes a stent graft and a thermal stent graft cutter for shortening the stent graft to a desired length in vivo. The thermal stent graft cutter is coupled to at least one of a stent graft cover at a distal longitudinal end of a cover body thereof, and the inner lumen tip of an inner lumen. A safety system allows activation of the stent graft cutter only when the stent graft is suitably sandwiched between the inner lumen tip and the distal end of the stent graft cover to inhibit inadvertent activation of the cutter and provide for proper cutting of the stent graft.

19 Claims, 13 Drawing Sheets

STENT GRAFT DELIVERY SYSTEM INCLUDING STENT GRAFT CUTTER

FIELD

The present technology is generally related to a stent graft delivery system including a stent graft cutter.

BACKGROUND

A number of vascular devices have been developed for replacing, supplementing, or excluding portions of blood vessels. These vascular devices include endoluminal vascular prostheses and stent grafts. Aneurysm exclusion devices are used to exclude vascular aneurysms and provide a prosthetic lumen for the flow of blood. Vascular aneurysms (abnormal dilation of a blood vessel) are usually the result of disease or a genetic predisposition, which can weaken the arterial wall and allow it to expand. Aneurysms can occur in any blood vessel, but most occur in the aorta and peripheral arteries, with the majority of aneurysms occurring in the abdominal aorta or the aortic arch. An abdominal aortic aneurysm typically begins below the renal arteries and extends into one or both of the iliac arteries. A thoracic aortic aneurysm typically occurs in the ascending or descending aorta.

Stent grafts for use in aortic aneurysms typically include a support structure supporting woven or interlocked graft material. Examples of woven graft materials are woven polymer materials, e.g., Dacron, or polytetrafluoroethylene (PTFE). Interlocked graft materials include knit, stretch, and velour materials. The graft material is secured to the inner or outer diameter of the support structure, which supports the graft material and/or holds it in place against a vessel wall. The stent graft is secured to a vessel wall above and below the aneurysm. An open crown without the graft material can be located above the aneurysm to provide a radial force to engage the vessel wall and seal the stent graft to the vessel wall.

SUMMARY

In one aspect, the present disclosure provides a stent graft delivery system. The stent graft delivery system comprises an inner lumen including an elongate inner lumen body and an inner lumen tip at a distal longitudinal end of the inner lumen body. A stent graft is positionable over the inner lumen. A stent graft cover is slidably positionable over the stent graft and the inner lumen. The stent graft cover is configured to retract proximally to expose a longitudinal portion of the stent graft. The stent graft cover includes an elongate cover body having a distal longitudinal end. A thermal stent graft cutter is coupled to the stent graft cover at the distal longitudinal end of the cover body and is configured to selectively generate and direct heat distally outward from the distal longitudinal end of the cover body to circumferentially cut the stent graft and shorten the length of the stent graft to a desired length.

In another aspect, the disclosure provides a stent graft delivery system. The stent graft delivery system comprises an inner lumen including an elongate inner lumen body and an inner lumen tip at a distal longitudinal end of the inner lumen body. A stent graft is positionable over the inner lumen. A stent graft cover is slidably positionable over the stent graft and the inner lumen. The stent graft cover is configured to retract proximally to expose a longitudinal portion of the stent graft. The stent graft cover includes an elongate cover body having a distal longitudinal end. A thermal stent graft cutter is coupled to the inner lumen and configured to selectively generate and direct heat from inner lumen tip to circumferentially cut the stent graft and shorten the length of the stent graft to a desired length.

In yet another aspect, the disclosure provides a method of delivering a stent graft to a treatment site within a subject. The method comprises inserting an assembled stent graft delivery system into a lumen of a subject. The assembled stent graft delivery system comprises: an inner lumen including an elongate inner lumen body and an inner lumen tip at a distal longitudinal end of the inner lumen body; a stent graft positionable over the inner lumen; a stent graft cover slidably positionable over the stent graft and the inner lumen; and a thermal stent graft cutter coupled to at least one of the stent graft cover at a distal longitudinal end of the cover body and the inner lumen tip. The stent graft cover is retracted to expose a longitudinal portion of the stent graft. The thermal stent graft cutter is activated to generate and direct heat to circumferentially cut the stent graft outside the stent graft cover and shorten the length of the stent graft to a desired length.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

The present disclosure relates to a stent graft delivery system including a stent graft and a stent graft cutter that is configured to allow a user to selective shorten, if desired, a stent graft to a desired length in vivo or in vitro. While these systems and methods are suitable for use in treating abdominal aortic aneurysms and thoracic aortic aneurysms (broadly, treatment sites), those skilled in the art will appreciate that the stent graft delivery system and teachings herein could be used to deliver other types of stent grafts for other vessels as well.

In general, described embodiments of the stent graft delivery system include an inner lumen or shaft (may also be referred to as a runner) having a tip, a stent graft positionable over the inner lumen, and a stent graft cover having a distal longitudinal end and being slidably positionable over the stent graft. In one or more embodiments, a stent graft cutter (e.g., a thermal cutter) is disposed at the distal longitudinal end of the stent graft cover and/or at the inner lumen tip so that cutting of the stent graft to its desired length is performed outside or inside the stent graft cover. In one or more embodiments, the inner lumen tip is used during the cutting operation to sandwich the stent graft between the inner lumen tip and the distal longitudinal end of the stent graft cover. In one more embodiments, a safety system is configured to detect a parameter of the inner lumen tip relative to the distal longitudinal end of the stent graft cover and determine when it is suitable to allow operation of the cutter to cut the stent graft to a desired length.

Stent Graft Cutter on Distal Longitudinal End of Stent Graft Cover

Figure 1:
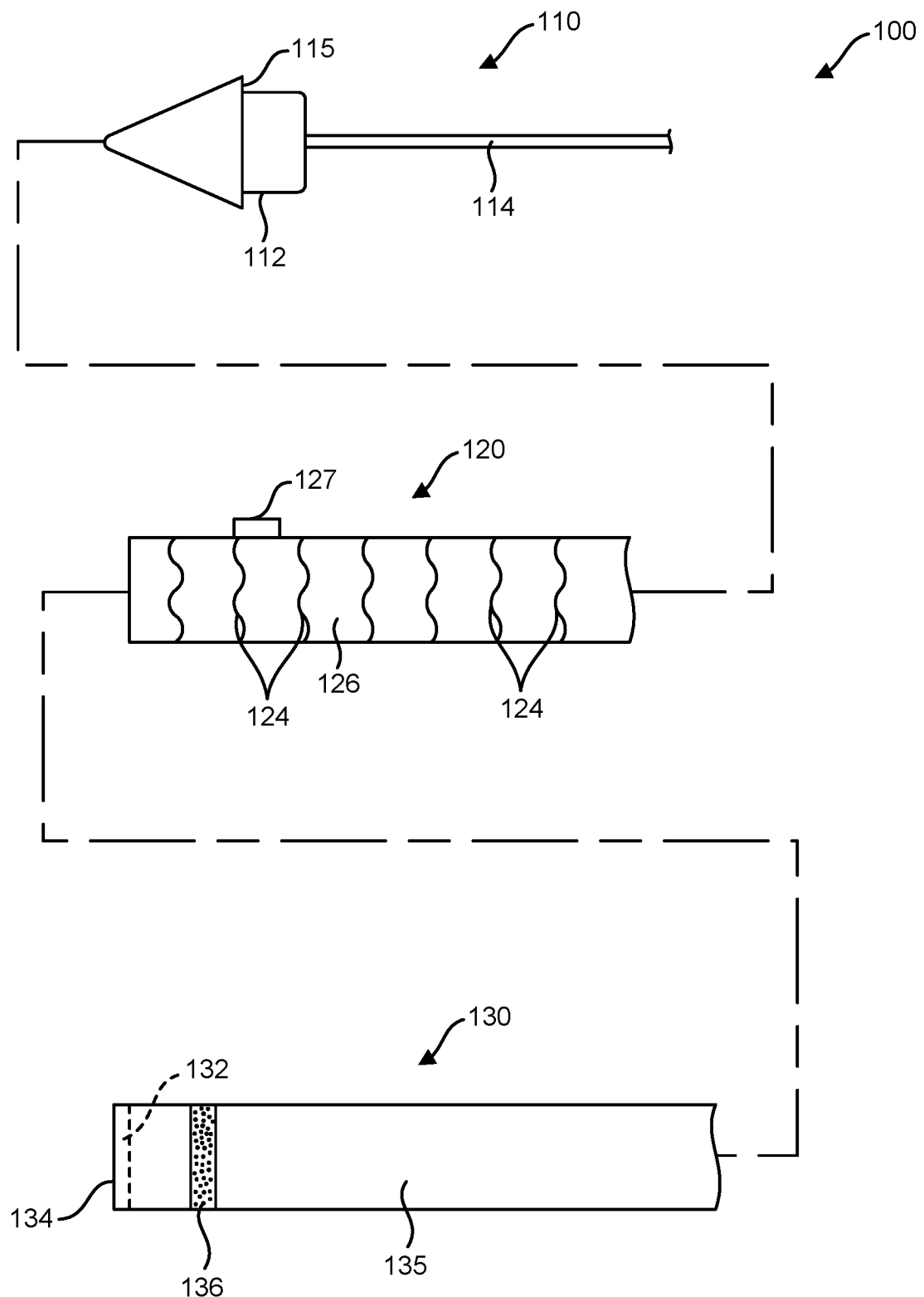
FIG. 1 is a schematic illustration of one embodiment of a stent graft delivery system of the present disclosure, including an inner lumen, a stent graft cover, and a stent graft removed from one another.

Referring to FIG. 1, one embodiment of a stent graft delivery system is generally indicated at reference numeral 100. The stent graft delivery system 100 includes an inner lumen, generally indicated at 110; a stent graft, generally indicated at 120, positionable over the inner lumen, and a stent graft cover, generally indicated at 130, slidably positionable over the stent graft 120. The stent graft delivery system 100 further includes a stent graft cutter 132 configured to selectively cut the stent graft 120 to shorten the length of the stent graft in vivo to a desired length. In one embodiment, a stent graft cutter 132 is located at a distal longitudinal end, generally indicated at 134, of an elongate body 135 of the stent graft cover 130. In another embodiment, a stent graft cutter 132' is located within an elongate body 135' of a stent graft cover 130'. In at least one embodiment, the stent graft cutter 132, 132' is a thermal cutter which produces heat of a suitable temperature to cut (e.g., melt) the stent graft 120 and fuse the cut end of the stent graft. As explained in more detail below, the inner lumen 110 may facilitate cutting of the stent graft 120.

Figure 3:
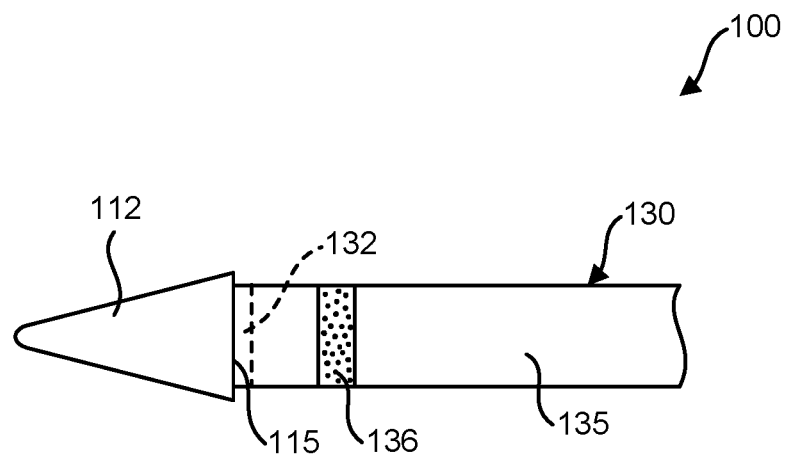
FIG. 3 is a schematic illustration of a distal longitudinal portion of the stent graft delivery system as assembled.

Referring to FIGS. 1 and 3, the inner lumen 110 supports the stent graft 120 so that the stent graft can be delivered to a treatment site in a vessel. In one embodiment, the inner lumen 110 includes an inner lumen nose or tip 112 at a distal end of an elongate inner lumen body 114. The illustrated inner lumen tip 112 tapers distally to facilitate passage through a vessel. In one example, the inner lumen tip 112 has a distal longitudinal portion and a proximal longitudinal portion. A maximum outer diameter of the distal longitudinal portion being greater than the proximal longitudinal portion to define a proximally-facing shoulder 115. In another example, such as shown in FIGS. 9-13, the proximal longitudinal portion may be omitted, however, the inner lumen tip still defines a proximally-facing shoulder at the juncture of the inner lumen body 114 and the inner lumen tip at a proximal longitudinal end of the tip. The shoulder 115 is configured to oppose and/or substantially abut the distal longitudinal end 134 of the stent graft cover 130, as shown in FIG. 3, when the inner lumen 110 is in its fully retracted position.

The inner lumen body 114 is long enough to reach from the treatment site in the vessel to the clinician. In one embodiment, the inner lumen 110 can include a guide wire lumen. The inner lumen 110 can be made of a single material, or the inner lumen nose 112 and the inner lumen body 114 can be made of different materials. The inner lumen 110 can be made of flexible biocompatible materials. For example, the inner lumen 110 can be made of polyurethane, polyethylene, PEBAX, nylon, or the like. The inner lumen nose 112 can include a radiopaque additive to provide the clinician with a visible tip when using fluoroscopy guidance to deliver the stent graft within the patient. As described below, for example, the inner lumen 110 can include an electrical conductor to electrically connect the thermal cutter 132, 132' to a power source.

Figure 4:
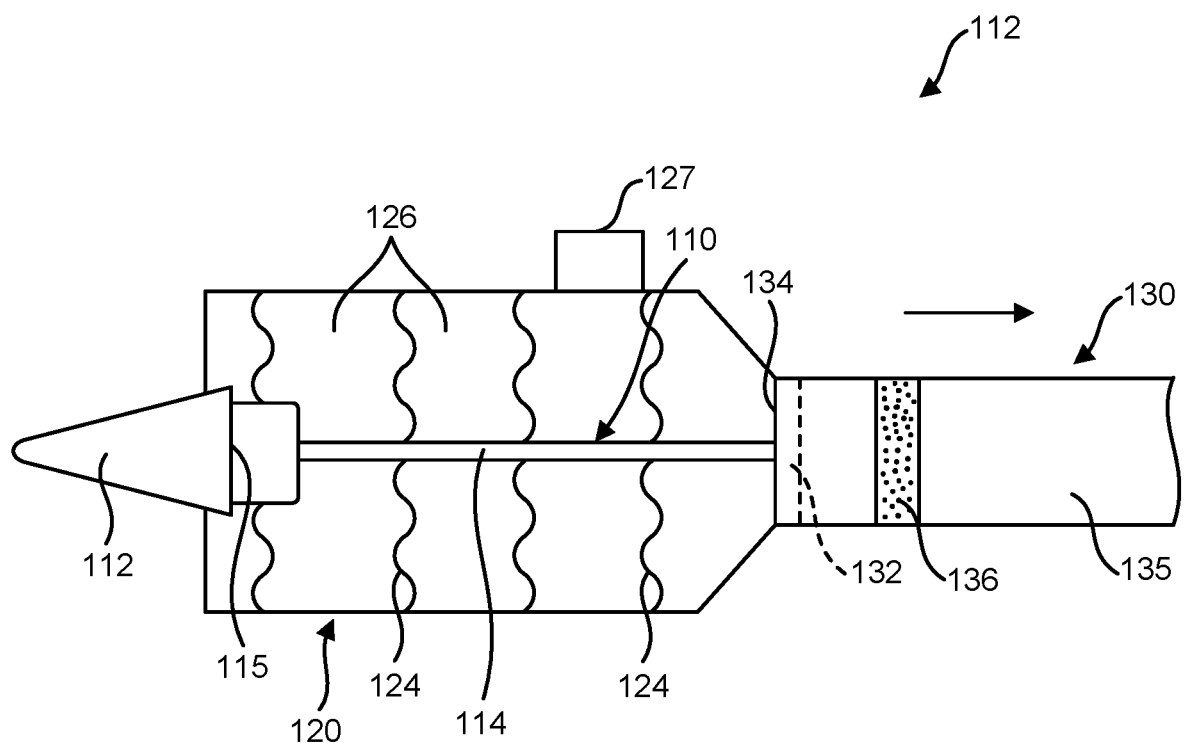
FIG. 4 is a schematic illustration of a distal longitudinal portion of the stent graft delivery system showing the stent graft cover being retracted to expose and allow expansion of the stent graft.

Referring to FIGS. 1 and 4, the stent graft 120 includes radially expandable stents 124 (or struts) spaced apart from one another along a length of the stent graft, and graft material 126 supported by the stents 124. In FIG. 3, the stent graft 120 is shown in its non-expanded or collapsed configuration, generally as it would be configured within the stent graft cover 130. As shown in FIG. 4, withdrawing or retracting the stent graft cover 130 relative to the stent graft 120 allows an exposed portion of the stent graft to radially expand to its expanded configuration. Non-stented portions 127 are portions of the stent graft 120 without stents 124 (e.g., longitudinally extending between adjacent stents and extending circumferentially around the circumference of the stent graft). Any of the non-stented portions 122 can be cut with the stent graft cutter 134 to shorten the length of the stent graft 120.

In this example, the stent graft 120 is a single tube with regularly spaced stents 124. The single tube can be the main stent graft or can be an iliac limb, an aorta extender cuff, or an iliac extender cuff. The stent graft can be of other types and configurations. In another embodiment, the stents 124 of the stent graft blank 120 are irregularly spaced. In another embodiment, the stent graft 120 is a bifurcated tube. In another embodiment, the stent graft 120 includes a bare spring extending distally beyond the graft material 126 to provide a radial force which engages the vessel wall and seals the stent graft at the vessel wall.

In general, the stent graft 120 can be any suitable a tubular graft configured to expand open and be in sealing contact with tissue after being implanted at the treatment site, such as in the abdominal aorta, thoracic aorta, or other vessel. In one such example, the stent graft 130 may be inserted into the target vessel, positioned across a lesion, and then expanded to bypass the weakened wall of the vessel, thereby preventing rupture of an aneurysm. The stent graft is in contact with the healthy tissue after implantation of the stent graft. The stent graft generally extends across the aneurysm in a vessel to divert flow through the stent graft and relieve the pressure normally applied to the weak aneurysmal wall.

The size and configuration of the stents 124 of the stent graft 120 depend upon the size and configuration of the vessel to be treated. Some of the individual stents 124 can be connected to each other by articulated or rigid joints as long as non-stented portions are provided. The length of the stent graft blank 120 may be the length of the aneurysm across which the stent graft will be implanted plus an additional remainder to assure that the stent graft blank 120 is longer than the aneurysm.

The stents 124 can be self-expanding. The stents 124 can be made of can be made of spring steel, stainless steel, titanium, nickel titanium alloys (Nitinol), a polymer or copolymer, a combination of these materials, or other suitable materials. The graft material 126 can be any woven or interlocked graft material suitable for stent grafts, such as woven polymer materials, e.g., Dacron polyester, or polytetrafluoroethylene (PTFE), or interlocked graft materials including knit, stretch, and velour materials. In some embodiments, the graft material 126 includes components made of collagen, albumin, an absorbable polymer, or biocompatible fiber. Alternatively, the graft material 126 is constructed from one or more suitable plastic or non-biodegradable materials.

Figure 2:
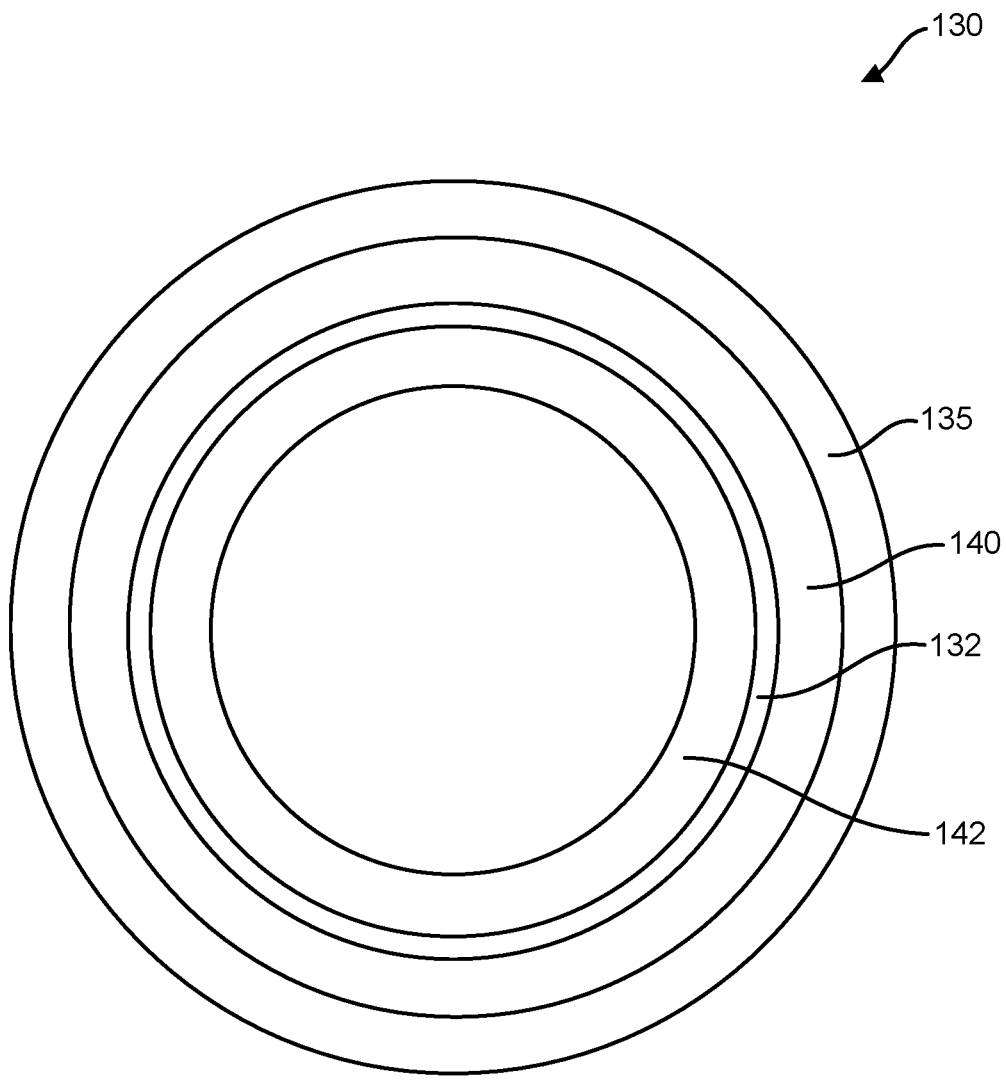
FIG. 2 is an enlarged schematic illustration of a distal longitudinal portion of the stent graft cover.

Referring to FIG. 1-3, the body 135 of the stent graft cover 130 is an elongate tube which retains and/or compresses the stent graft blank 120 on the inner lumen 110 when the stent graft blank 120 is being delivered to the treatment site in the patient. The stent graft cover 130 is then retracted to allow the exposed portion of the stent graft 120 to expand at the treatment site. The stent graft cover 130 may include a radiopaque marker 136 adjacent the distal longitudinal end 134 to locate the stent graft cover 130 in the vasculature and locate the stent graft cutter 132 relative to the stent graft 120. The body 135 of the stent graft cover 130 can be made of flexible biocompatible materials. For example, the body 135 can be made of polyurethane, polyethylene, PEBAX, nylon, or the like.

Figure 8:
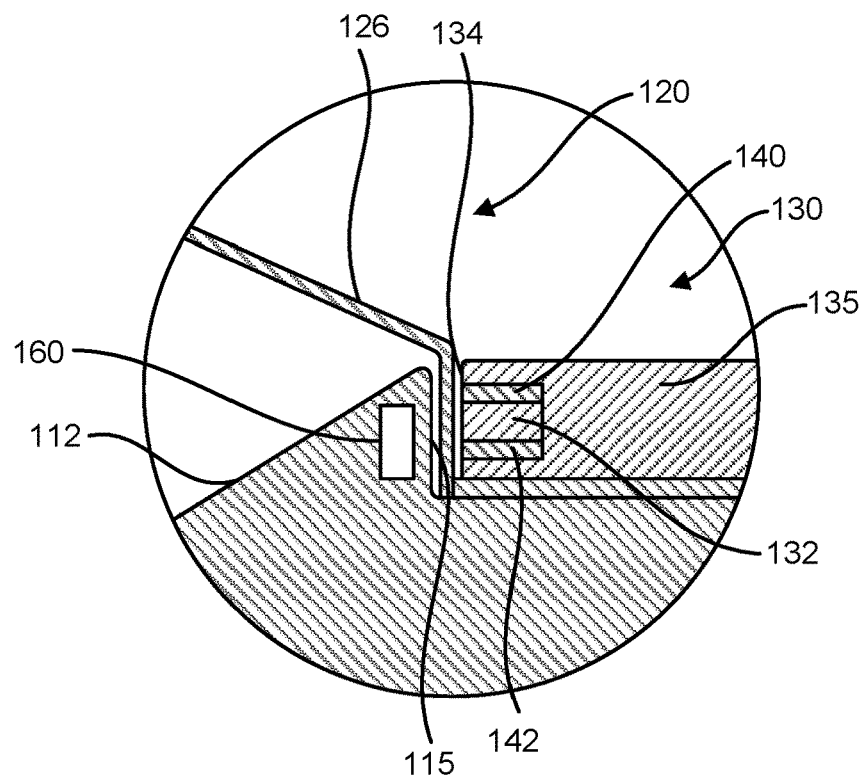
FIG. 8 is an enlarged detail view as indicated in FIG. 7.
Figure 9:
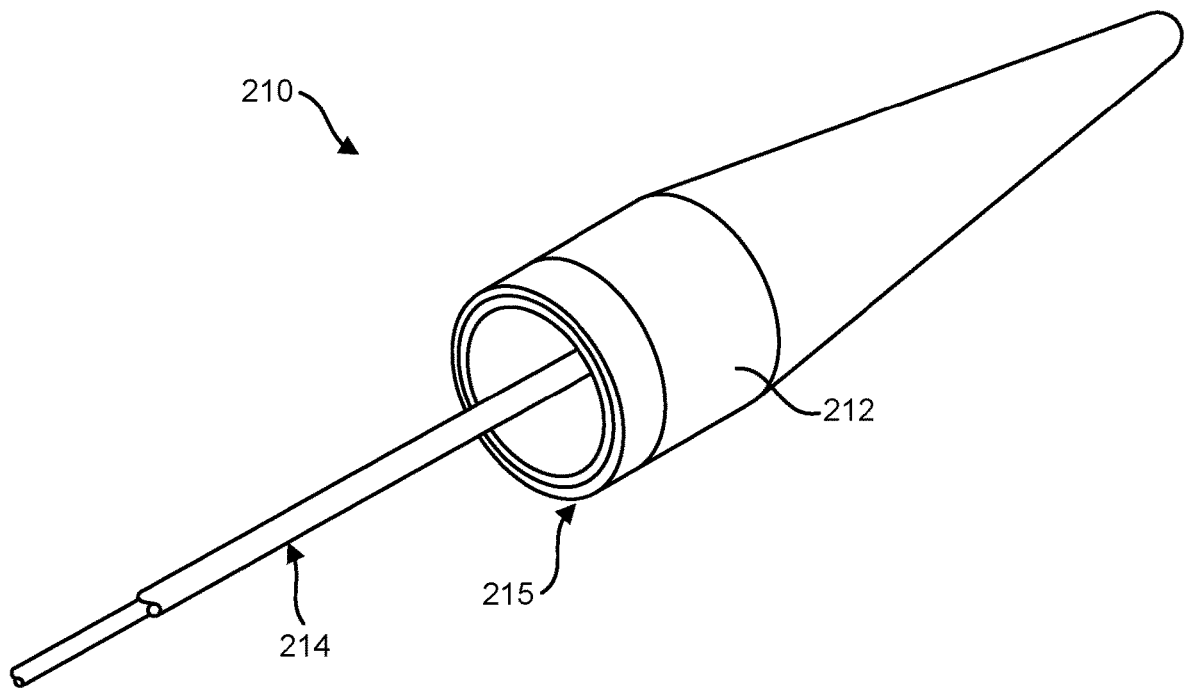
FIG. 9 is a schematic illustration of a distal longitudinal portion of an inner lumen of another embodiment of a stent graft delivery system of the present disclosure.

Referring to FIGS. 1 and 2, the stent graft cutter 132 disposed within the body 135 of the stent graft cover 130 is used to cut the stent graft 120 to the desired length to form the stent graft. The stent graft cutter 132 is located on the inside circumference of the stent graft cover 130 and its distal end is uncovered by or exposed through the distal longitudinal end 134 of the body 135, as shown in FIG. 2. The stent graft cutter 132 can be molded into the stent graft cover 130 or attached to the stent graft cover 130 with an adhesive. The adhesive can be any biocompatible, thin, high bonding adhesive. As shown in FIGS. 2 and 8, an insulating layer 140 (e.g., an annular insulating layer) comprising an insulator can be placed between the stent graft cutter 132 and the body 135 of the stent graft cover 130 to protect the stent graft cover 130 from heat from the stent graft cutter 132 during cutting. Another insulating layer 142 can overlie a radially inner surface of the cutter 132 to protect the inner lumen 110, specifically the inner lumen body, disposed within the stent graft cover 120 radially adjacent the cutter 132. The insulating layer 142 may be omitted or configured to allow inner circumferential cutting by the cutter 132. This inner circumferential cutting of the cutter 132 may be in addition to or in combination with distal end cutting of the cutter. In one embodiment, a polyxylene polymer such as Parylene can be used as the insulator of the insulating layers 140, 142. The insulator can also be used around the distal end of the stent graft cutter 132 to control and direct the heat from the stent graft cutter 132 distally outward from the cutter. For example, the insulator can cover most of the stent graft cutter 132, such as 80 percent of the surface area of the distal end, leaving a small ring of the stent graft cutter 132 exposed, such as 20 percent of the surface area. The small ring which is exposed provides the heat to cut the stent graft 120, as explained below.

The stent graft cutter 132 can be formed of any material which can generate sufficient heat to cut the stent graft 120, and more specifically, the graft material 126. The stent graft cutter 132 can be a single piece or multiple turns of wire. In one embodiment, the stent graft cutter 132 is heated with a radiofrequency (RF) source, such as an RF source delivering 180 to 300 Watts, applying a radiofrequency beam to the stent graft cutter 132 from outside the patient. The stent graft cutter 132 can be made of any material that can be heated by RF, such as metal or ceramic composites. For example, the stent graft cutter 132 can be made of Nitinol, stainless steel, or the like. In another embodiment, the stent graft cutter 132 is heated with an electrical current source electrically connected to the stent graft cutter 132 passing an electric current through the stent graft cutter 132. The current source 150 (FIG. 14) can be provided in the handle 151 (shown schematically in FIG. 14), whereby electrical conductors (e.g., wires or metal bands) run along the stent graft cover 130 to the cutter 132. Activation of the current source 150 can be controlled by a controller 152 (e.g., microprocessor control), and the practitioner can communicate with the controller via an actuator 154 on the handle 151. The stent graft cutter 132 can be made of any material that can be heated with an electrical current, such as metal or ceramic composites. For example, the stent graft cutter 132 can be made of Nitinol, stainless steel, nichrome, or the like, and the current source can be an electrocautery power supply. The combination of stent graft cutter 132 and graft material can be selected so that the stent graft cutter 132 seals the edge of the graft material when making the cut. Cutting is initiated by the energization of the stent graft cutter 132 so that it is heated to circumferentially melt the adjacent graft material that is disposed distally of the cutter.

Figure 5:
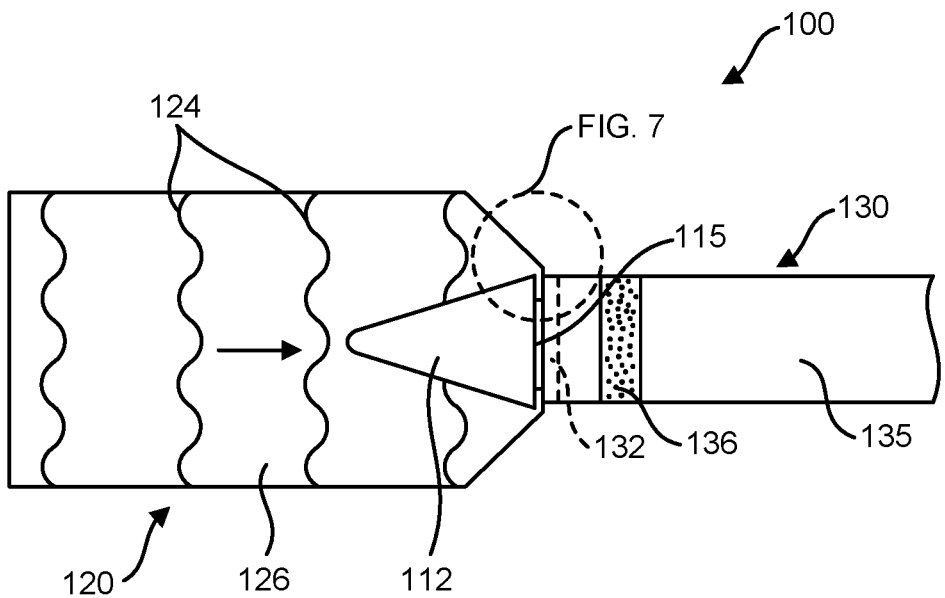
FIG. 5 is similar to FIG. 4, except showing the inner lumen in a retracted configuration and an inner lumen tip generally abutting a distal longitudinal end of the stent graft cover.
Figure 6:
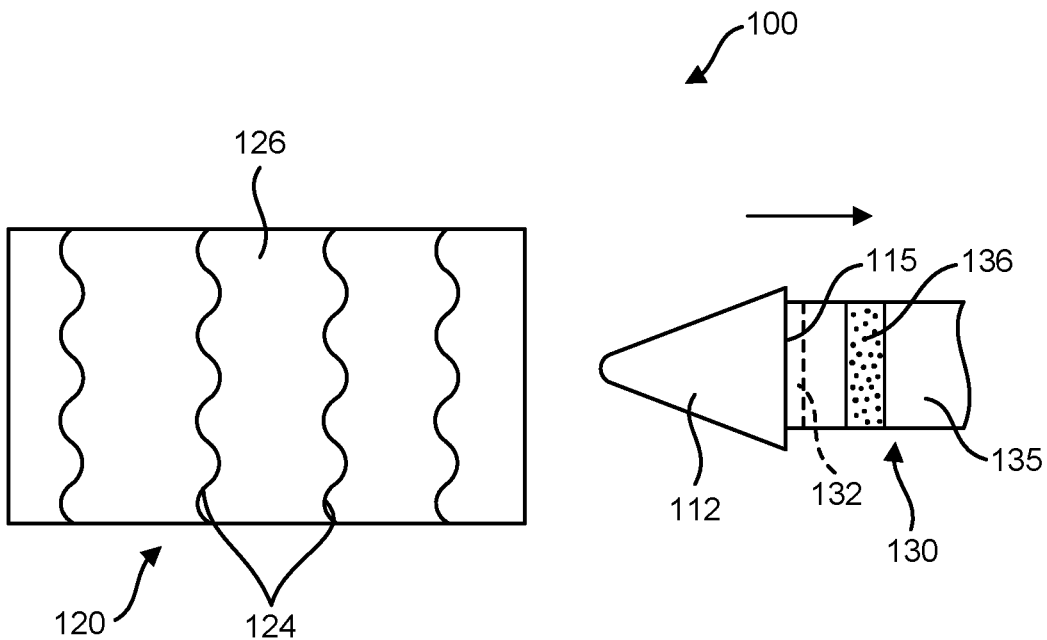
FIG. 6 is similar to FIG. 5, except showing the inner lumen and the stent graft cover being removed from the expanded stent graft.
Figure 7:
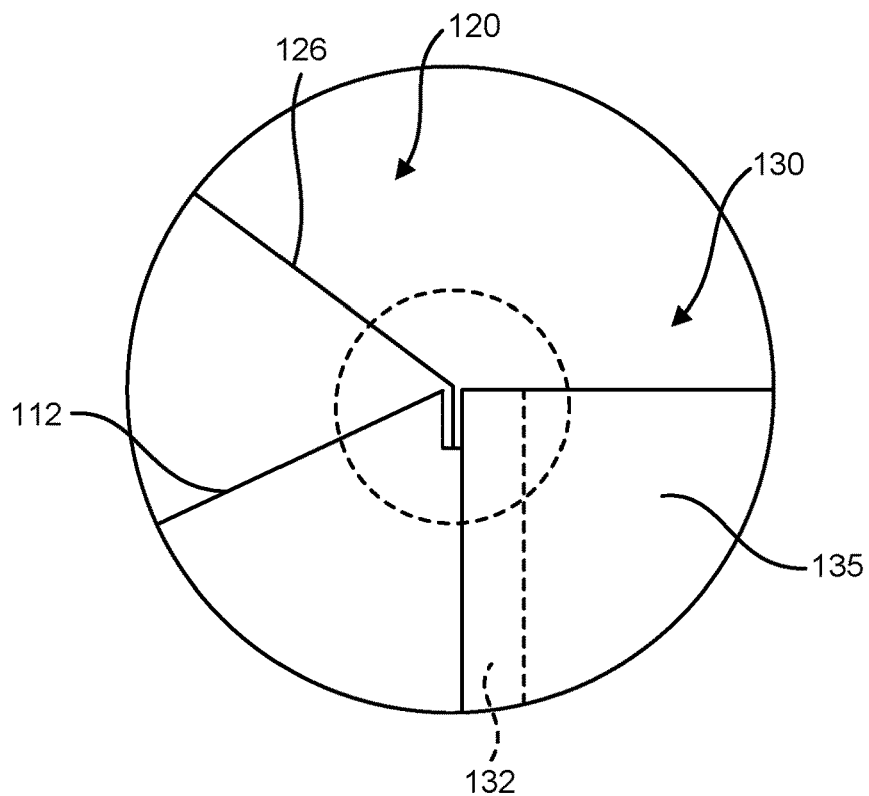
FIG. 7 is an enlarged detail view as indicated in FIG. 5.

One method of using the stent graft delivery system 100 will now be described with reference to FIGS. 3-6 for illustrative purposes. The stent graft delivery system 100, such as assembled in FIG. 3, is delivered to the treatment site. A guidewire (not shown) may be used to deliver the stent graft delivery system 100 to the site. After positioning the stent graft delivery system 100 at the treatment site, the practitioner retracts the stent graft cover 130 relative to the stent graft 120 and the inner lumen 110 to expose the stent graft and allow it to expand within the treatment site, as shown in FIG. 4. An actuator at a handle (not shown) outside the subject may be used to retract the stent graft cover 130. After determining when a desired length of the stent graft 120 is expanded at the treatment site, the practitioner retracts the inner lumen 110 within the stent graft cover and relative to the stent graft, as shown in FIG. 5. The tip 112 of the inner lumen 110 is retracted through the expanded stent graft 120 until it reaches the distal longitudinal end 134 of the stent graft cover 130, whereby a circumferential portion of the stent graft, more specifically a circumferential portion of the non-stented portion 127, is disposed between the shoulder 115 of the tip and the stent graft cutter 132 at the distal longitudinal end of the stent graft cover, as shown in FIGS. 7 and 8. The shoulder 115 of the tip 112 may press the stent graft 120 against the distal longitudinal end of the stent graft cover 130 outside of the stent graft cover. The stent graft cutter 132 is then activated to circumferentially cut the stent graft 120 outside of the stent graft cover 130. For example, in the illustrated embodiment the thermal stent graft cutter 132 is activated, such as by activating electrical current source 150 via the actuator 154, to heat the stent graft cutter. As shown in FIG. 6, once the stent graft 120 is cut, the expanded stent graft is released from the stent graft cover 130, and the inner lumen 110 and the stent graft cover 130 are retracted together, leaving the expanded stent graft at the treatment site within the patient. In another example, as mentioned above, the stent graft cutter may be disposed within the stent graft cover. In the embodiment shown in FIGS. 15 and 16, the stent graft cover 130' includes an internal shoulder 133 at the intersection of proximal and distal inner surfaces 137, 139, respectively, where an inner diameter at the proximal inner surface is less than an inner diameter at the distal inner surface. When the inner lumen tip 112' is retracted, the stent graft 120 is sandwiched between a proximal shoulder 141 (e.g., proximal longitudinal end) of the inner lumen tip and the internal shoulder 133 of the stent graft cover 130'. As illustrated in FIG. 16, the stent graft cutter 132' (e.g., an annular thermal cutter) may be disposed adjacent the proximal inner surface 139 of the stent graft cover 130' to cut a circumferential portion of the stent graft 120 disposed between the outer diameter of the inner lumen tip 112' and the proximal inner surface of the stent graft cover. Alternatively, as also illustrated in FIG. 16, the stent graft cutter 132' may be disposed adjacent the internal shoulder 133 of the stent graft cover 130' to cut a circumferential portion of the stent graft 120 disposed between the proximal shoulder 141 (e.g., proximal longitudinal end) of the inner lumen tip 112' and the internal shoulder. The stent graft cutter 132' may be disposed at other locations.

Safety System for Stent Graft Cutter

In one or more embodiments, the stent graft delivery system includes a safety system configured to allow activation of the stent graft cutter only when the stent graft is suitably sandwiched between the inner lumen tip and the distal end of the stent graft cover to inhibit inadvertent activation of the cutter and provide for proper cutting of the stent graft. In the illustrated embodiment, a safety system is incorporated in the illustrated stent graft delivery system 100. The safety system may be incorporated in other stent graft delivery systems utilizing other stent graft cutting arrangement and configurations. For example, the safety system can be incorporated into the stent graft delivery system described below. It is understood that the safety system may have other configurations and/or designs configured to determine when the stent graft is suitably sandwiched between the inner lumen tip and the distal end of the stent graft cover.

Figure 14:
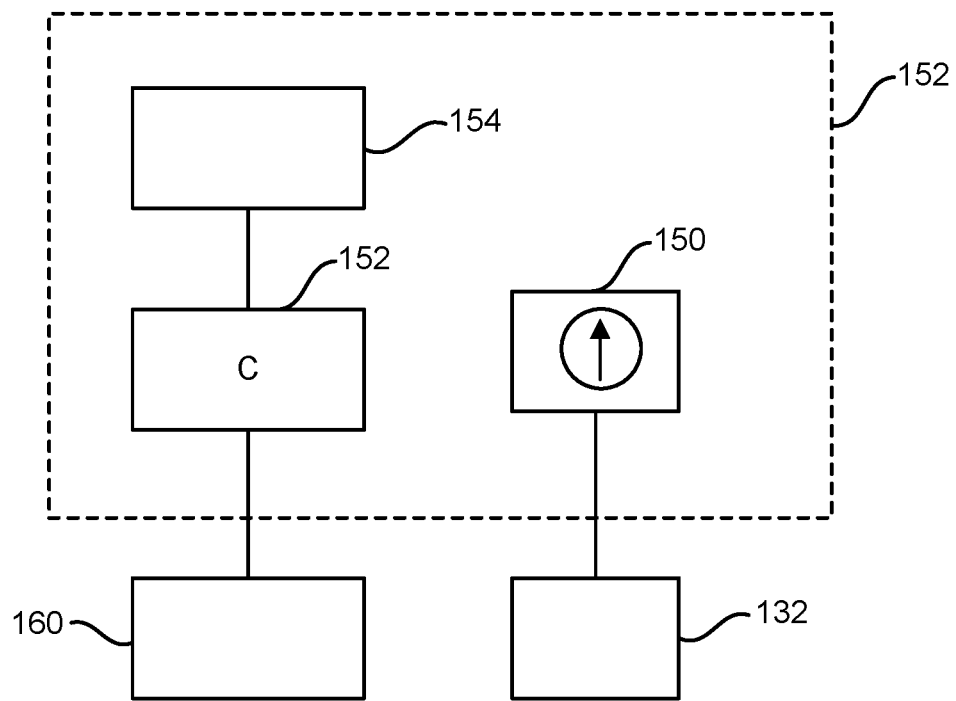
FIG. 14 is a control diagram of one embodiment of a stent graft delivery system of the present disclosure.

In one of the illustrated embodiments, shown in FIGS. 8 and 14, the safety system includes at least one sensor 160 (e.g., a proximity sensor or pressure sensor) on either or both of the inner lumen tip 112 and the distal longitudinal end 134 of the stent graft cover 130. For example, in this illustrated embodiment, the sensor is mounted on or in (broadly, coupled to) the inner lumen tip 112. As shown in FIG. 14, the sensor 160 is in communication with (e.g., wired or wireless) the controller 152, which can be housed in the handle. The controller 152 is configured to receive the signal from the sensor 160 and determine whether the stent graft 120 is suitably sandwiched between the inner lumen tip 112 and the distal longitudinal end 134 of the stent graft cover 130 based on the received signal. If the controller 152 determines the stent graft 120 is suitably sandwiched between the inner lumen tip 112 (e.g., the shoulder 115) and the distal longitudinal end 134 of the stent graft cover 130 based on the received signal, then the controller is configured to allow activation of the stent graft cutter 132.

In one example, the sensor 160 is a proximity sensor configured to provide a signal to the controller 152 indicative of the proximity of the sensor and the inner lumen tip 112 (e.g., the shoulder 115 of the inner lumen tip) to the distal longitudinal end 134 of the stent graft cover 130 (e.g., the stent graft cutter 132). When the sensor 160 is a predetermined longitudinal distance from the distal longitudinal end of the stent cover 130, the signal generated by the sensor 160 and received by the controller 152 is indicative of the stent graft 120 being suitable for cutting, for example, the stent graft is suitably sandwiched between the inner lumen tip 112 and the distal longitudinal end 134 of the stent graft cover 130 or the inner lumen tip is suitably disposed within the stent graft cover 130. In another example, the sensor 160 is a pressure sensor configured to provide a signal to the controller 152 indicative of the inner lumen tip 112 (e.g., the shoulder 115 of the inner lumen tip) applying pressure to the distal longitudinal end 134 of the stent graft cover 130 (e.g., the stent graft cutter 132). When the inner lumen tip 112 is applying a predetermined pressure against the distal longitudinal end 134 of the stent cover 130, the signal generated by the sensor 160 and received by the controller 152 is indicative of the stent graft 120 being suitably sandwiched between the inner lumen tip and the distal end of the stent graft cover. In another embodiment, the sensor 160 may be an impedance sensor or another sensor.

Figure 15:
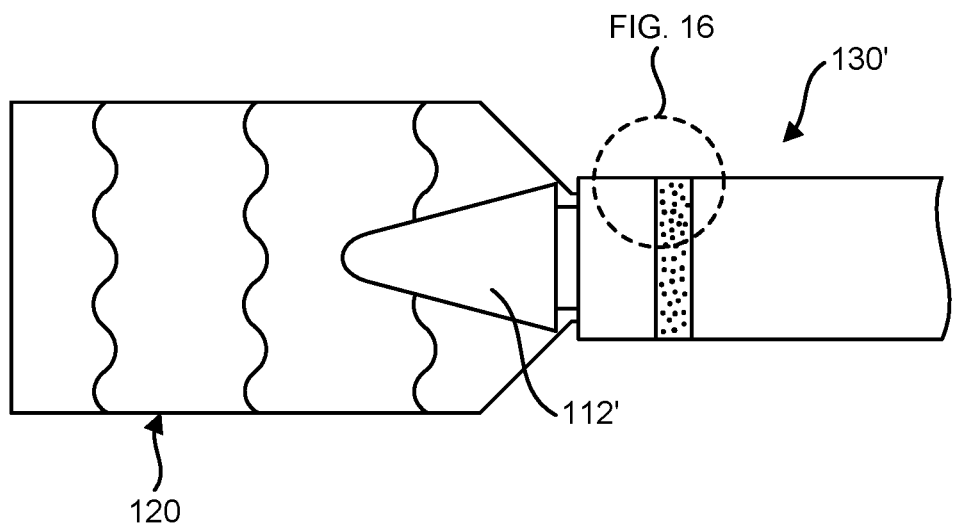
FIG. 15 is schematic illustration of another embodiment of a stent graft delivery system showing an inner lumen in a retracted configuration and an inner lumen tip generally abutting a distal longitudinal end of a stent graft cover.
Figure 16:
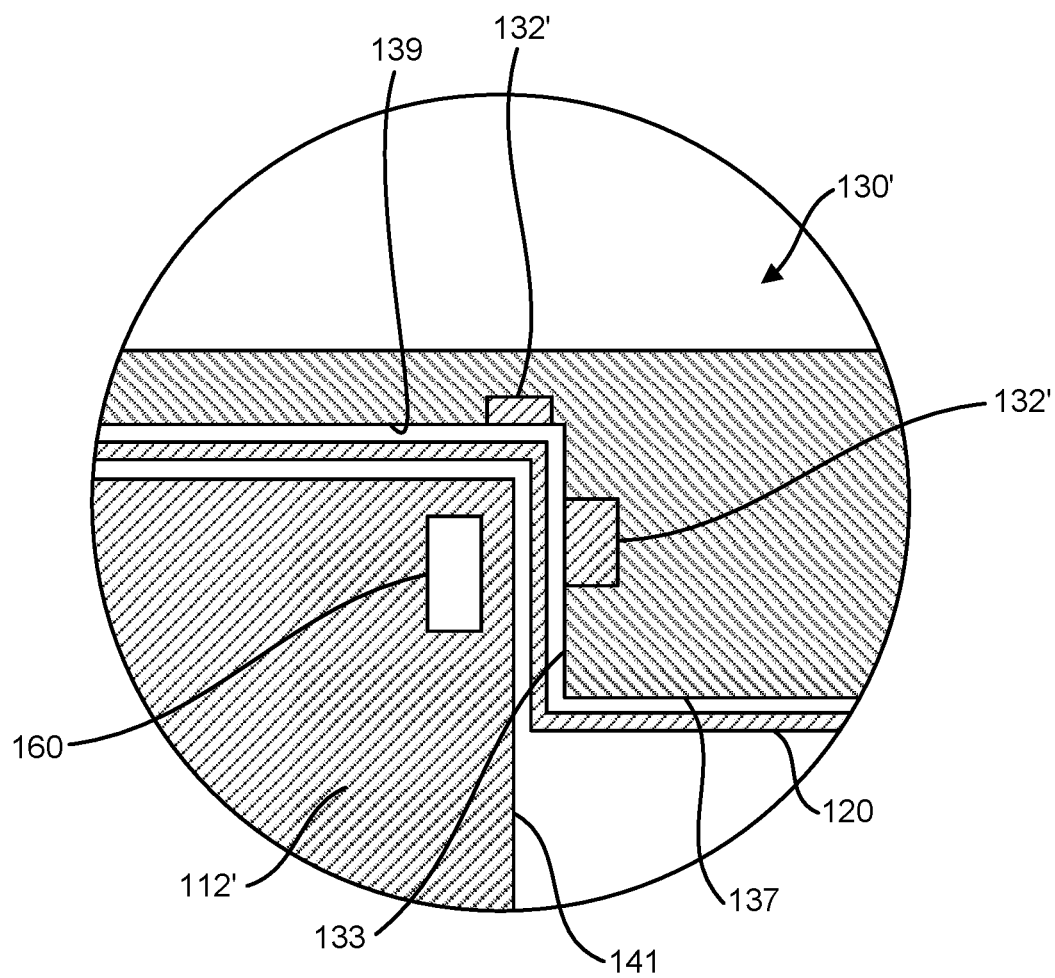
FIG. 16 is an enlarged, detail cross section of the stent graft delivery system as indicated in FIG. 15.

In the example shown in FIGS. 15 and 16, the sensor 160 may be disposed adjacent the proximal shoulder 141 (e.g., proximal longitudinal end) of the inner lumen tip 112'. The operation of the sensor 160 may be substantially the same as described above. As an example, the sensor 160 may be configured to indicate to the controller 152 when the inner lumen (e.g., inner lumen tip 112') is suitably disposed within the stent graft cover 130' to allow for suitable cutting. For example, the sensor 160 may indicate to the controller 152 when the stent graft 120 is sandwiched between the inner lumen tip 112' and the inner surface (e.g., one of the inner surfaces 139, 137) of the stent graft cover 130'.

The safety system may be incorporated in other stent graft delivery systems utilizing other stent graft cutting arrangement and configurations. For example, the safety system can be incorporated into the stent graft delivery system described below. It is understood that the safety system may have other configurations and/or designs configured to determine when the stent graft is suitably sandwiched between the inner lumen tip and the distal end of the stent graft cover.

Figure 19:
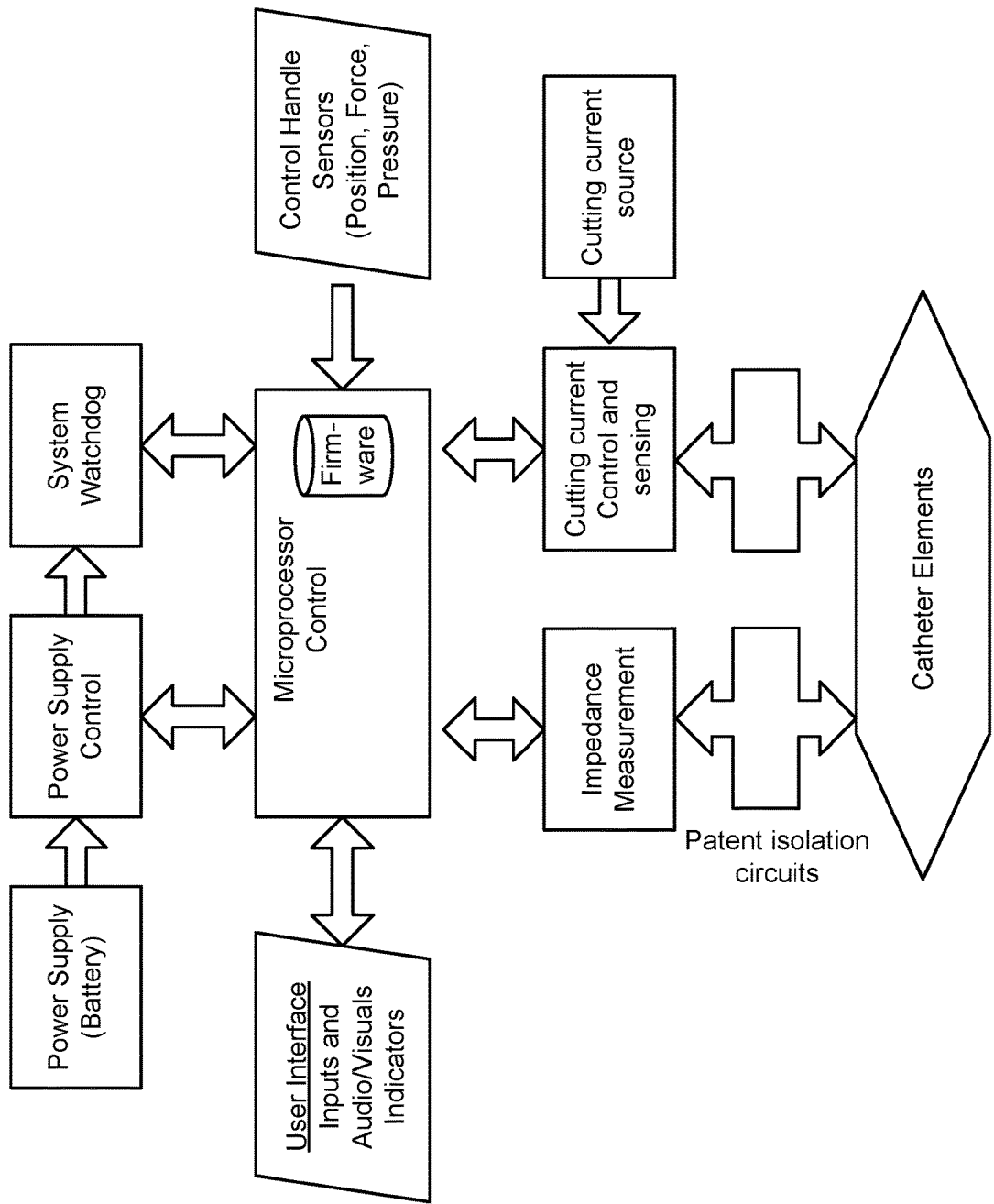
FIG. 19 is a schematic illustration of another embodiment of an inner lumen for a stent graft delivery system.

A suitable diagram of control system for at least one embodiment of the stent graft delivery system is shown in FIG. 19.

Stent Graft Cutter on Inner Lumen Tip

Figure 13:
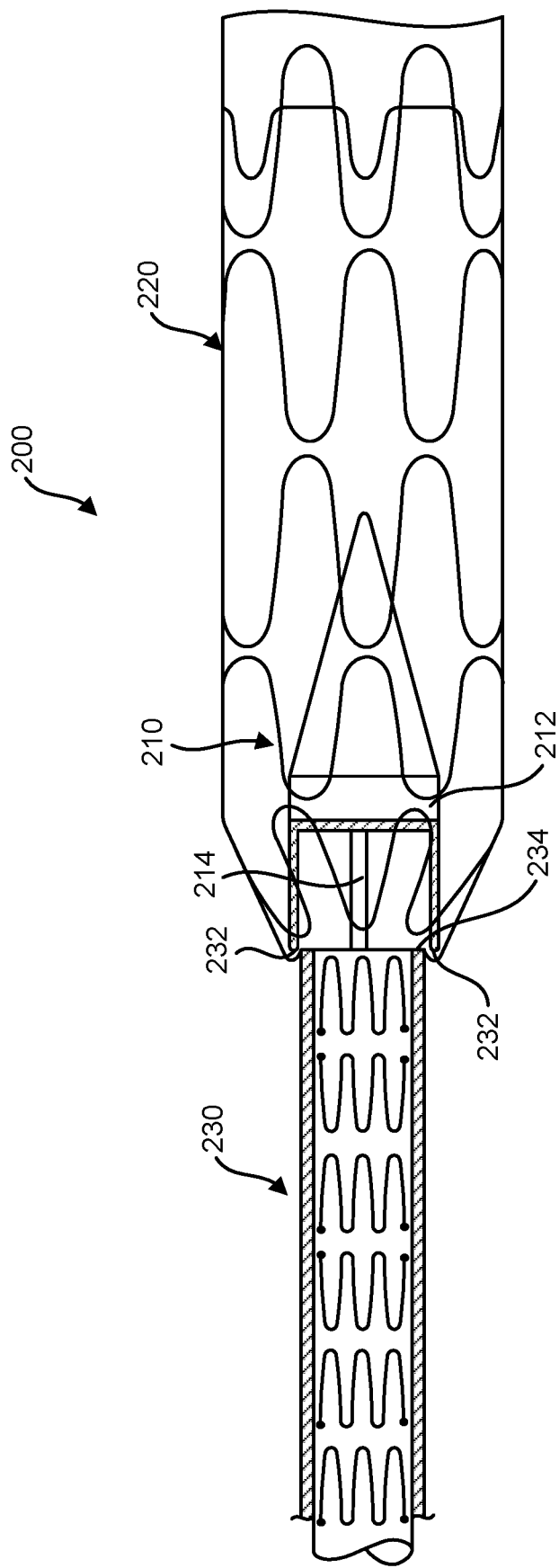
FIG. 13 is a schematic illustration of a distal longitudinal portion of the stent delivery graft showing the stent graft cover retracted to expose and allow expansion of the stent graft, the inner lumen in a retracted configuration, and the inner lumen tip generally abutting a distal longitudinal end of the stent graft cover, the proximal longitudinal portion of the inner lumen tip being show in section (the layers of the inner lumen tip not being shown for ease of illustration).

Referring to FIG. 13, another embodiment of a stent graft delivery system is generally indicated at reference numeral 200. The stent graft delivery system 200 includes an inner lumen 210, a stent graft 220 positionable over the inner lumen, and a stent graft cover 230 slidably positionable over the stent graft 220. In FIG. 13, the stent graft delivery system 200 is shown with the stent graft cover 230 retracted to expose and allow expansion of the stent graft 220, the inner lumen 210 in a retracted configuration, and the inner lumen tip 212 generally abutting a distal longitudinal end 234 of the stent graft cover 230 (transparent), and the proximal longitudinal portion of the inner lumen tip being show in section. Other than the differences described hereinafter, the stent graft delivery system may be the same as the stent graft delivery system described above, with the same or like component being indicated by the corresponding reference numerals plus 100.

The main difference between the two embodiments of the stent graft delivery system is that the stent graft cutter 232 of the present stent graft delivery system 200 is located on the inner lumen tip 212 rather than at the distal longitudinal end 234 of the stent graft cover 230. Like the first embodiment, the illustrated stent graft cutter 232 is a thermal cutter which produces high temperature heat to cut the stent graft 220. In the illustrated embodiment, the thermal cutter 232 general opposes the distal longitudinal end 234 of the stent graft cover 230. As an example, the thermal cutter 232 may be at the shoulder 215 of the inner lumen tip 212, which may be at the proximal end of the inner lumen tip, such as shown in FIGS. 9-13, or at an intermediate longitudinal location, such as shown in the first embodiment of the stent graft delivery system described above.

Figure 10:
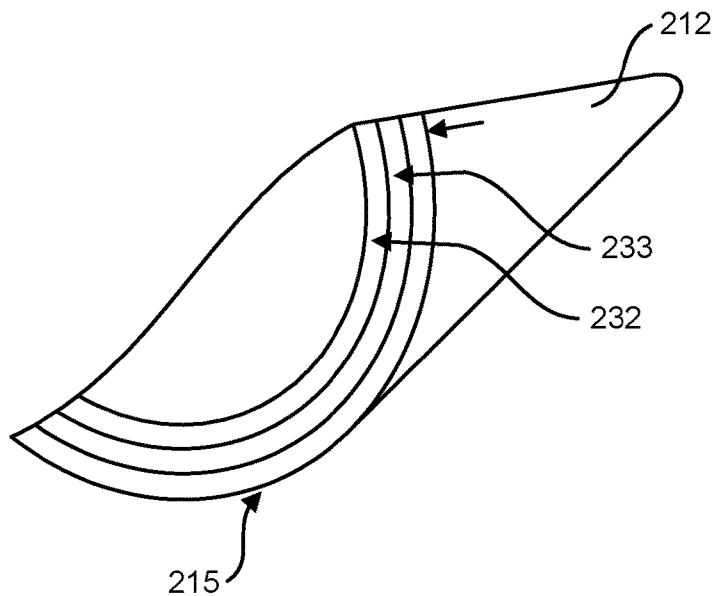
FIG. 10 is an enlarged, fragmentary detail view of a tip of the inner lumen of FIG. 9.
Figure 11:
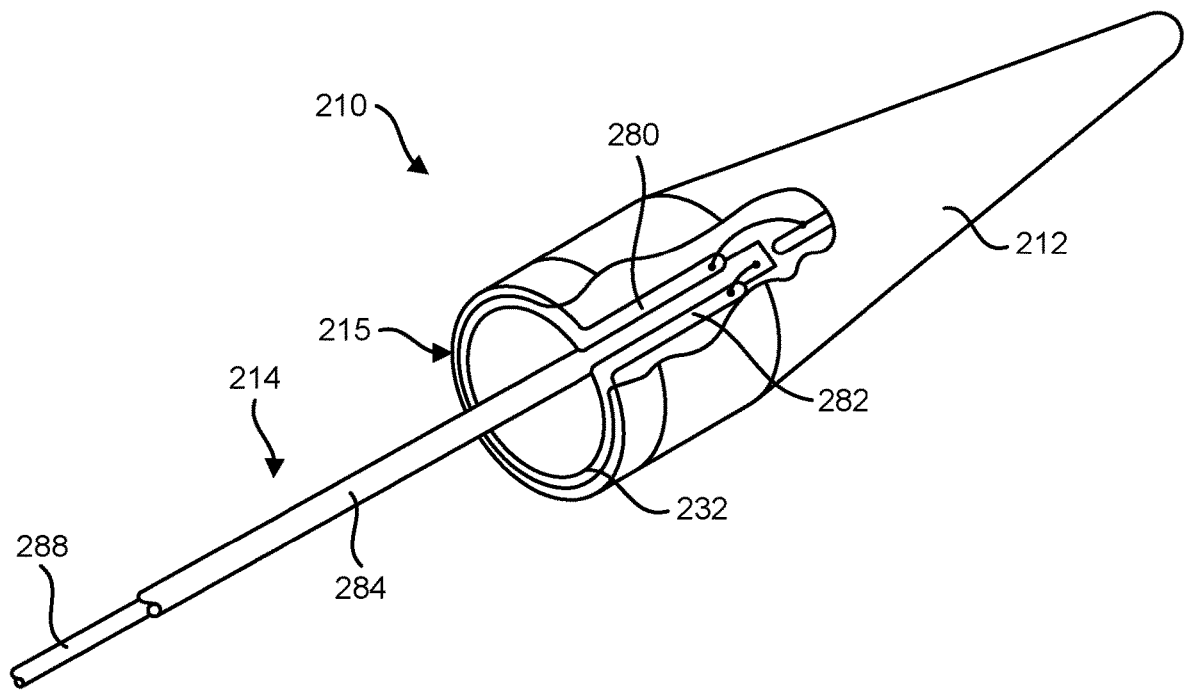
FIG. 11 is similar to FIG. 9, except having a portion of the inner lumen tip broken away to show internal components.
Figure 12:
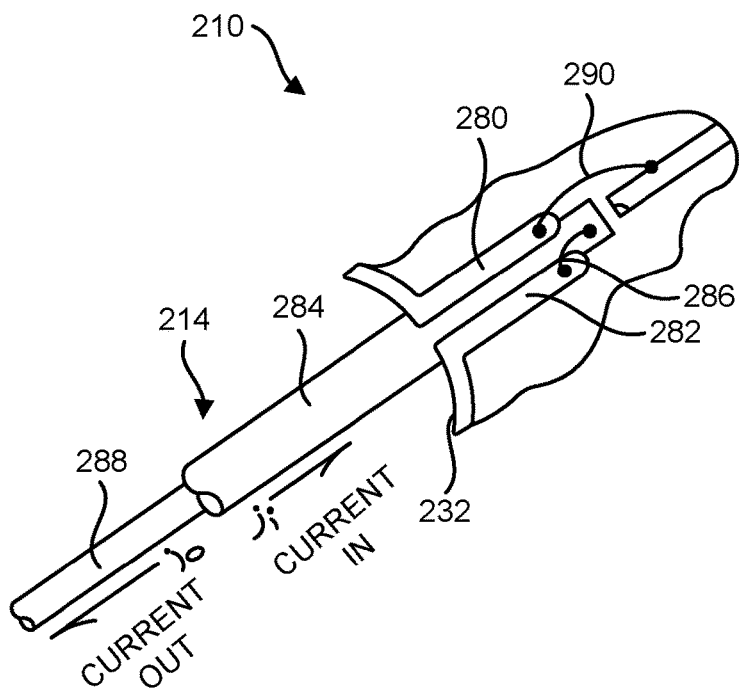
FIG. 12 is an enlarged, fragmentary view of FIG. 11.

Referring to FIGS. 9-12, the illustrated cutter 232 includes an annular cutter body within the inner lumen tip 212. As shown in FIG. 10, an annular layer 233 of insulation may be disposed radially between the cutter 232 and the inner lumen tip 212. Positive and negative terminals 280, 282 extend longitudinally from the annular cutter body and are electrically connected to respective conductors within the inner lumen tip. As an example, referring to FIG. 12, the elongate body 214 of the inner lumen 210 may include a first conductor 284 electrically connected to the negative terminal 282, such as by a jumper 286 or in other ways, and a second conductor 288 electrically connected to the positive terminal 280, such as by a jumper 290 or in other ways. The proximal ends of the first and second conductors 284, 288 can be electrically connected to the electrical current source 150, whereby current is selectively delivered to the thermal cutter 232 to activate cutting.

Referring to FIG. 13, the stent graft 220 may be selectively cut using the cutter 232 in a manner similar to the first embodiment of the stent delivery system 100 described above. In particular, after a desired length of the stent graft 220 is expanded at the treatment site, the inner lumen 210 is retracted to bring the inner lumen tip 212 to the distal longitudinal end 234 of the stent graft cover 230. When the stent graft 220 is sandwiched between the shoulder 215 of the inner lumen tip 212 (and the cutter 232) and the distal longitudinal end 234 of the stent graft cover 230, the cutter 232 may be activated by the practitioner to cut the stent graft. As described above, the stent graft delivery system 200 may include the safety system which is employed in a similar manner as described above.

Figure 17:
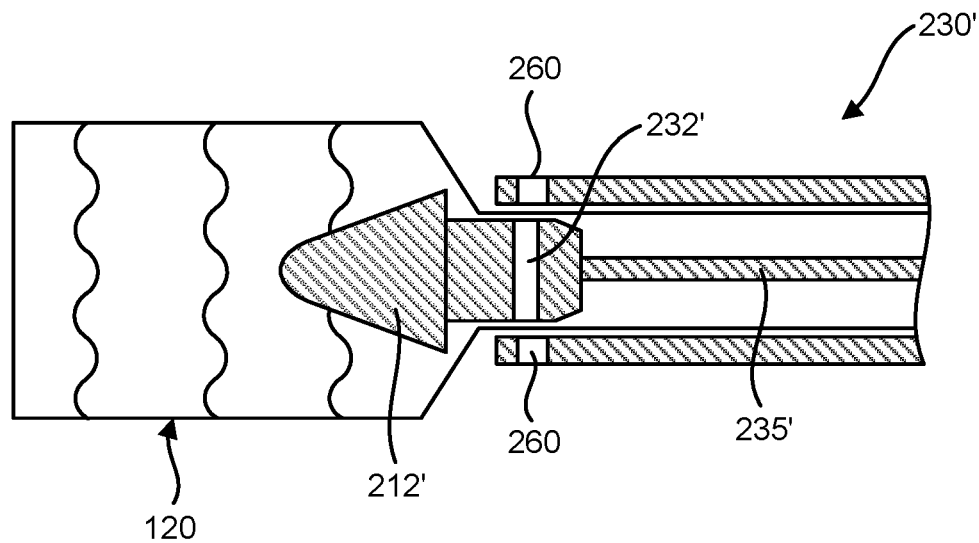
FIG. 17 is a schematic illustration of another embodiment of a stent graft delivery system shown in cross section.

As disclosed above, the thermal cutter may be disposed at other locations on the inner lumen. For example, in FIG. 17 a thermal cutter 232' is proximal of the shoulder 215 of the inner lumen tip 212', such as on the body 235' of the inner lumen or on a proximal portion of the inner lumen tip. In this embodiment, a sensor 260 may be disposed on the stent graft cover 230'. The sensor 260 is configured to be operated and used in the same manner as the sensor 160 described above.

Figure 18:
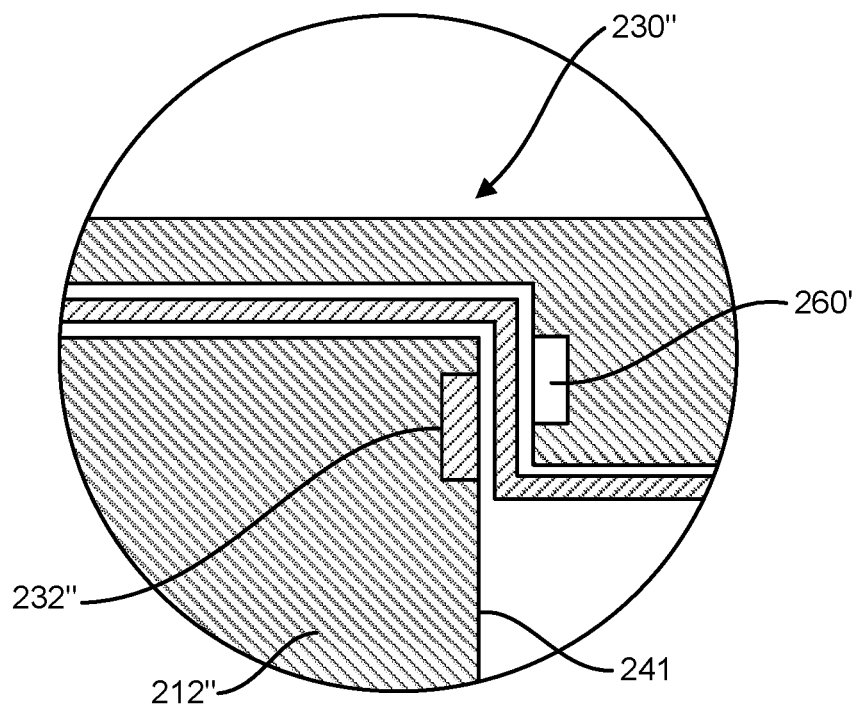
FIG. 18 is an enlarged, detail cross section of another embodiment of a stent graft delivery system.

In another example shown in FIG. 18, the thermal cutter 232" may be at the proximal shoulder 241 (e.g., proximal longitudinal end) of the inner lumen tip 212". This embodiment may be similar in construction and operation to the embodiment of FIGS. 15 and 16, except the thermal cutter 232" is on the inner lumen tip 212", adjacent the proximal shoulder 241, and the sensor 260' may be on the stent graft cover 230" adjacent the internal shoulder 233.

Figure 20:
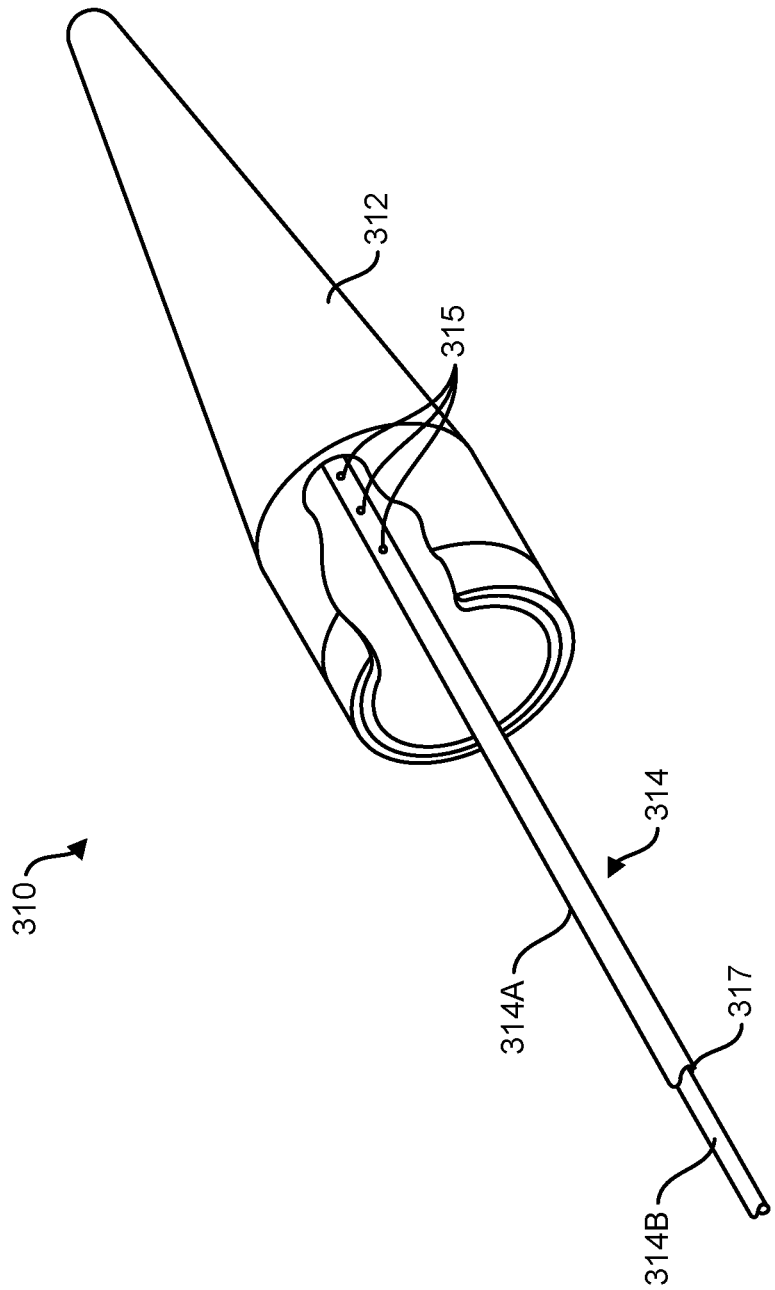
FIG. 20 is a diagram of an exemplary control system for a stent graft delivery system.

Referring to FIG. 20, another example of an inner lumen is generally indicated at reference numeral 310. The inner lumen 310 may be incorporated in any of the above-described stent graft delivery systems. The inner lumen 310 includes an elongate body 314 and an inner lumen tip 312 at a distal end of the elongate body. The inner lumen tip 312 may include the cutter or the cutter may be at other locations. The elongate body 314 includes an outer body portion 314A and an inner body portion 314B received in and extending along the outer body portion. The outer body portion 314A defines one or more openings 315 at a distal end portion thereof, such as within a space defined by a proximal end portion of the inner lumen tip 312. A plenum 317 for fluid (e.g., gas or liquid) defined by the elongate body 314 is in fluid communication with the openings 315. For example, the plenum 317 may be defined by the annular space between the inner body portion 314B and the outer body portion 314A. A proximal end of the plenum 317 is configured to be in fluid communication with a source of fluid (e.g., gas or liquid). For example, the source of fluid may be carbon dioxide or other gas soluble in blood or liquid. The gas, for example, escaping the openings 315 forces environmental fluid out of the immediate space around the area where the stent graft is clamped to facilitate a rapid temperature increase and sustained temperatures needed to complete the trimming operation.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more controllers, such as one or more digital signal processors (DSPs), general purpose microprocessors, application specific integrated circuits (ASICs), field programmable logic arrays (FPGAs), or other equivalent integrated or discrete logic circuitry. Accordingly, the term "controller" as used herein may refer to any of the foregoing structure or any other physical structure suitable for implementation of the described techniques. Also, the techniques could be fully implemented in one or more circuits or logic elements.

What is claimed is:

1. A stent graft delivery system comprising:
   an inner lumen including an elongate inner lumen body and an inner lumen tip at a distal longitudinal end of the inner lumen body;
   a stent graft positionable over the inner lumen;
   a stent graft cover slidably positionable over the stent graft and the inner lumen, the stent graft cover configured to retract proximally to expose a longitudinal portion of the stent graft, the stent graft cover including an elongate cover body having a distal longitudinal end; and
   a thermal stent graft cutter coupled to the stent graft cover at the distal longitudinal end of the cover body and configured to selectively generate and direct heat distally outward from the distal longitudinal end of the cover body to circumferentially cut the stent graft and shorten the length of the stent graft to a desired length,
   wherein the inner lumen tip includes a proximally facing shoulder with an outer diameter equal to or greater than an outer diameter of the stent graft cover such that the proximally facing shoulder faces the distal longitudinal end of the stent graft cover with the proximal facing shoulder positioned adjacent to the distal longitudinal end of the stent graft cover.

2. The stent graft delivery system set forth in claim 1, wherein the longitudinal portion of the stent graft exposed outside the stent graft cover is configured to radially expand.

3. The stent graft delivery system set forth in claim 2, wherein the inner lumen is configured to be retracted through the expanded longitudinal portion of the stent graft exposed outside the stent graft cover to a retracted position in which a circumferential portion of the stent graft cover is sandwiched between the proximally-facing shoulder of the inner lumen tip and the distal longitudinal end of the stent graft cover.

4. The stent graft delivery system set forth in claim 3, wherein the proximally-facing shoulder of the inner lumen tip is configured to press the sandwiched circumferential portion of the stent graft against the thermal stent graft cutter.

5. The stent graft delivery system set forth in claim 4, further comprising a safety system including a sensor configured to detect a parameter relating to a relationship between the inner lumen tip and the distal longitudinal end of the stent graft cover.

6. The stent graft delivery system set forth in claim 5, wherein the sensor is coupled to at least one of the inner lumen tip and the stent graft cover.

7. The stent graft delivery system set forth in claim 6, wherein the safety system further includes a controller in communication with the sensor, wherein the controller is configured to receive the signal from the sensor and determine whether the stent graft is suitably sandwiched between the inner lumen tip and the distal longitudinal end of the stent graft cover based on the received signal.

8. A stent graft delivery system comprising:
   an inner lumen including an elongate inner lumen body and an inner lumen tip at a distal longitudinal end of the inner lumen body;
   a stent graft positionable over the inner lumen;
   a stent graft cover slidably positionable over the stent graft and the inner lumen, the stent graft cover configured to retract proximally to expose a longitudinal portion of the stent graft, the stent graft cover including an elongate cover body having a distal longitudinal end, wherein the longitudinal portion of the stent graft exposed outside the stent graft cover is configured to radially expand, wherein the inner lumen is configured to be retracted through the expanded longitudinal portion of the stent graft exposed outside the stent graft cover to a retracted position in which a circumferential portion of the stent graft is sandwiched between the inner lumen tip and the distal longitudinal end of the stent graft cover;
   a thermal stent graft cutter coupled to the stent graft cover at the distal longitudinal end of the cover body and configured to selectively generate and direct heat distally outward from the distal longitudinal end of the cover body to circumferentially cut the stent graft and shorten the length of the stent graft to a desired length; and
   a safety system including a sensor configured to detect a parameter relating to a relationship between the inner lumen tip and the distal longitudinal end of the stent graft cover and a controller in communication with the sensor, wherein the controller is configured to:
      receive the signal from the sensor and determine whether the stent graft is suitably sandwiched between the inner lumen tip and the distal longitudinal end of the stent graft cover based on the received signal;
      allow activation of the thermal stent graft cutter if the controller determines the stent graft is suitably sandwiched between the inner lumen tip and the distal longitudinal end of the stent graft cover based on the received signal; and
      inhibit activation of the thermal stent graft cutter if the controller determines the stent graft is not suitably sandwiched between the inner lumen tip and the distal longitudinal end of the stent graft cover based on the received signal.

9. The stent graft delivery system set forth in claim 8, wherein the sensor comprises a proximity sensor.

10. The stent graft delivery system set forth in claim 8, wherein the sensor comprises a pressure sensor.

11. A method of delivering a stent graft to a treatment site within a subject, the method comprising:
    inserting an assembled stent graft delivery system into a lumen of a subject, wherein the assembled stent graft delivery system comprises:
       an inner lumen including an elongate inner lumen body and an inner lumen tip at a distal longitudinal end of the inner lumen body;
       a stent graft disposed over the inner lumen, the stent graft including a plurality of radially expandable stents longitudinally spaced apart along a length of the stent graft, and graft material supported by the stents, the graft material forming non-stented portions longitudinally extending between adjacent stents and extending circumferentially continuously around the circumference of the stent graft;
       a stent graft cover slidably disposed over the stent graft and the inner lumen; and
       a thermal stent graft cutter coupled to at least one of the stent graft cover at a distal longitudinal end of the stent graft cover and the inner lumen tip;
    retracting the stent graft cover to expose a longitudinal portion of the stent graft;
    activating the thermal stent graft cutter to generate and direct heat to circumferentially cut the graft material of the stent graft outside the stent graft cover and shorten the length of the stent graft to a desired length.

12. The method of claim stent graft delivery system set forth in claim 11, wherein retracting the stent graft cover to expose a longitudinal portion of the stent graft causes the longitudinal portion of the stent graft exposed outside the stent graft cover to radially expand.

13. The method of claim 12, further comprising retracting the inner lumen through the expanded longitudinal portion of the stent graft exposed outside the stent graft cover to a retracted position in which a circumferential portion of the graft material of the stent graft is sandwiched between the inner lumen tip and the distal longitudinal end of the stent graft cover.

14. The method of claim 12, further comprising retracting the inner lumen through the expanded longitudinal portion of the stent graft exposed outside the stent graft cover to a retracted position in which a circumferential portion of the stent graft material of the graft material of the stent graft is sandwiched between a proximally-facing shoulder of the inner lumen tip and the distal longitudinal end of the stent graft cover.

15. The method of claim 14, further comprising pressing the sandwiched circumferential portion of the stent graft material against the thermal stent graft cutter with the proximally-facing shoulder of the inner lumen tip.

16. The method of claim 13, further comprising detecting a parameter relating to a relationship between the inner lumen tip and the distal longitudinal end of the stent graft cover to determine if the stent graft material is properly located between the inner lumen tip and the distal longitudinal end of the stent graft cover.

17. The method of claim 16, wherein detecting a parameter comprises a sensor coupled to at least one of the inner lumen tip and the stent graft cover detecting the parameter.

18. The method of claim 17, further comprising a controller receiving a signal from the sensor and determining whether the stent graft material is suitably sandwiched between the inner lumen tip and the distal longitudinal end of the stent graft cover based on the received signal.

19. The method of claim 18, further comprising:
the controller allowing activation of the thermal stent graft cutter if the controller determines the stent graft material is suitably sandwiched between the inner lumen tip and the distal longitudinal end of the stent graft cover based on the received signal; and
the controller inhibiting activation of the thermal stent graft cutter if the controller determines the stent graft material is not suitably sandwiched between the inner lumen tip and the distal longitudinal end of the stent graft cover based on the received signal.

* * * * *